United States Patent
Khan et al.

(10) Patent No.: US 9,656,049 B1
(45) Date of Patent: *May 23, 2017

(54) SUBCUTANEOUS FLUID PUMP

(71) Applicants: Mubashir H. Khan, Springfield, MO (US); Jesse G. Taylor, Springfield, MO (US); Qasim Khalil, Dayton, OH (US)

(72) Inventors: Mubashir H. Khan, Springfield, MO (US); Jesse G. Taylor, Springfield, MO (US); Qasim Khalil, Dayton, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/130,948

(22) Filed: Apr. 16, 2016

Related U.S. Application Data

(63) Continuation of application No. 14/019,000, filed on Sep. 5, 2013, now Pat. No. 9,339,636.

(60) Provisional application No. 61/743,527, filed on Sep. 6, 2012, provisional application No. 61/797,291, filed on Dec. 3, 2012, provisional application No. 61/744,177, filed on Sep. 20, 2012.

(51) Int. Cl.
| | |
|---|---|
| *A61M 5/00* | (2006.01) |
| *A61M 27/00* | (2006.01) |
| *A61M 1/12* | (2006.01) |
| *A61M 5/142* | (2006.01) |

(52) U.S. Cl.
CPC ............ *A61M 27/002* (2013.01); *A61M 1/12* (2013.01); *A61M 5/14276* (2013.01); *A61M 2210/1021* (2013.01)

(58) Field of Classification Search
CPC ............ A61M 27/002; A61M 5/14276; A61M 27/006; A61M 5/1723; A61M 2205/3355; A61M 2205/8287; A61M 2205/1085
USPC ........................................................ 604/8, 9
See application file for complete search history.

(56) References Cited

U.S. PATENT DOCUMENTS

| | | | |
|---|---|---|---|
| 1,169,475 A | 1/1916 | Finnigan ...................... | 361/147 |
| 3,089,064 A | 5/1963 | Cotton de Bennetot ..... | 361/147 |
| 3,370,538 A | 2/1968 | Hines ............................ | 417/322 |
| 3,503,400 A | 3/1970 | Osthagen et al. ............ | 604/249 |
| 3,527,220 A | 9/1970 | Summers ....................... | 128/260 |
| 3,585,648 A | 6/1971 | Suroff ........................... | 623/3.1 |
| 3,608,088 A | 9/1971 | Dorman et al. .............. | 623/3.13 |
| 3,768,931 A | 10/1973 | Willis, Jr. .................... | 417/322 |
| 3,810,259 A | 5/1974 | Summers ....................... | 3/1 |
| 3,924,631 A | 12/1975 | Mancusi, Jr. ................. | 128/346 |
| 3,939,821 A | 2/1976 | Roth ............................. | 128/1 R |

(Continued)

*Primary Examiner* — Phillip R Wiest
(74) *Attorney, Agent, or Firm* — Jonathan A. Bay

(57) ABSTRACT

A subcutaneous pump is provided to drain excess patient fluid from a first bodily location and discharge into a second bodily location. The pump is made from elongated flexible tube, an anchor, a check valve and then also magnetic or magnetizable material. The tube extends between a fenestrated intake end left loose in the first location (eg., peritoneal cavity) and a discharge end for the second location (eg., stomach or bladder). The anchor affixes the discharge end into the second location. The tube furthermore has a specified medial zone to be embedded in the subcutaneous layer of the patient's abdominal wall. The check valve is disposed inside the tube anywhere between the medial zone and the discharge end. The magnetic or magnetizable material is disposed in or around the specified medial zone and adapted to induce fluid pumping through the specified medial zone in response to an applied magnetic field.

16 Claims, 10 Drawing Sheets

(56) References Cited

U.S. PATENT DOCUMENTS

| | | | |
|---|---|---|---|
| 4,024,855 A | 5/1977 | Bucalo | 128/1 |
| 4,176,411 A | 12/1979 | Runge | 3/1.7 |
| 4,731,076 A | 3/1988 | Noon et al. | 623/3 |
| 4,784,646 A | 11/1988 | Feingold | 604/175 |
| 4,908,012 A | 3/1990 | Moise et al. | 600/16 |
| 5,129,789 A | 7/1992 | Thornton et al. | 417/53 |
| 5,167,615 A | 12/1992 | East et al. | 604/9 |
| 5,397,347 A | 3/1995 | Cuilleron et al. | 623/2 |
| 5,463,263 A | 10/1995 | Flynn | 310/181 |
| 5,643,194 A | 7/1997 | Negre | 604/8 |
| 5,762,599 A | 6/1998 | Sohn | 600/30 |
| 5,938,409 A | 8/1999 | Radle, Jr. et al. | 417/133 |
| 6,417,750 B1 | 7/2002 | Sohn | 335/207 |
| 6,450,173 B1 | 9/2002 | Forsell | 128/899 |
| 7,195,608 B2 | 3/2007 | Burnett | 604/9 |
| 7,311,690 B2 | 12/2007 | Burnett | 604/9 |
| 7,335,027 B1 | 2/2008 | Conti | 434/267 |
| 7,335,179 B2 | 2/2008 | Burnett | 604/9 |
| 7,621,886 B2 | 11/2009 | Burnett | 604/9 |
| 7,695,253 B2 | 4/2010 | Yang | 417/322 |
| 7,909,790 B2 | 3/2011 | Burnett | 604/9 |
| 8,038,641 B2 | 10/2011 | Soares et al. | 604/9 |
| 8,202,248 B2 | 6/2012 | Burnett et al. | 604/131 |
| 8,292,800 B2 | 10/2012 | Stone et al. | 600/37 |
| 8,394,048 B2 | 3/2013 | Burnett | 604/9 |
| 8,398,577 B2 | 3/2013 | Burnett | 604/9 |
| 8,398,617 B2 | 3/2013 | Ginggen et al. | 604/891.1 |
| 8,506,516 B2 | 8/2013 | Kassab et al. | 604/8 |
| 8,506,517 B2 | 8/2013 | Stergiopulos | 604/9 |
| 9,339,636 B1 * | 5/2016 | Khan | A61M 27/002 |
| 2009/0318844 A1 * | 12/2009 | Burnett | A61M 27/002 604/9 |
| 2010/0312163 A1 | 12/2010 | Forsell | 604/9 |
| 2011/0274566 A1 | 11/2011 | Amirouche et al. | 417/322 |
| 2011/0301408 A1 | 12/2011 | Augarten | 600/37 |

* cited by examiner

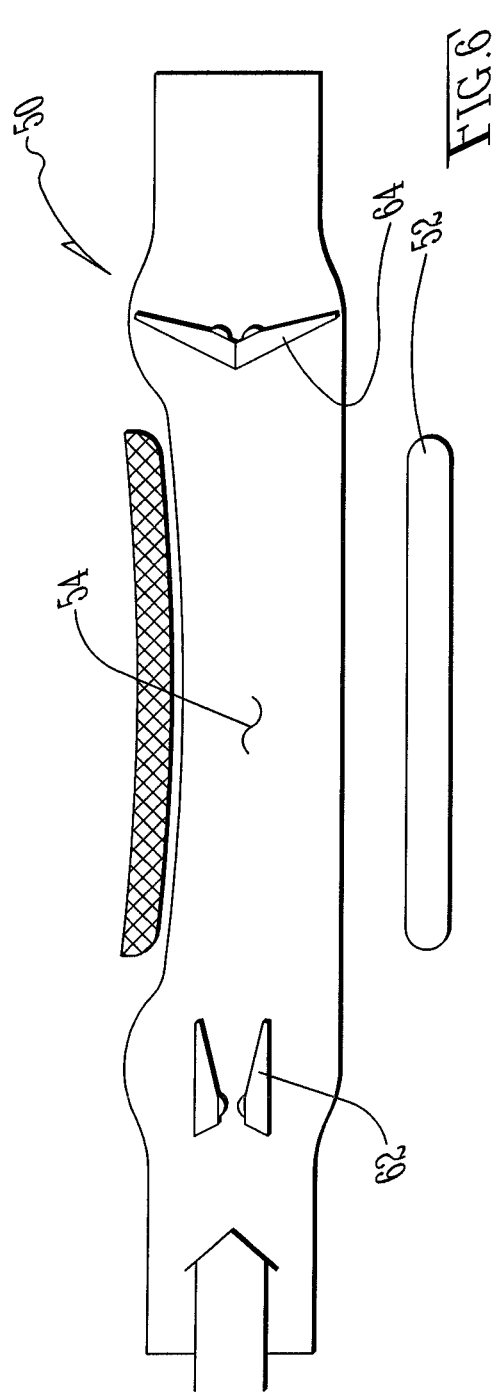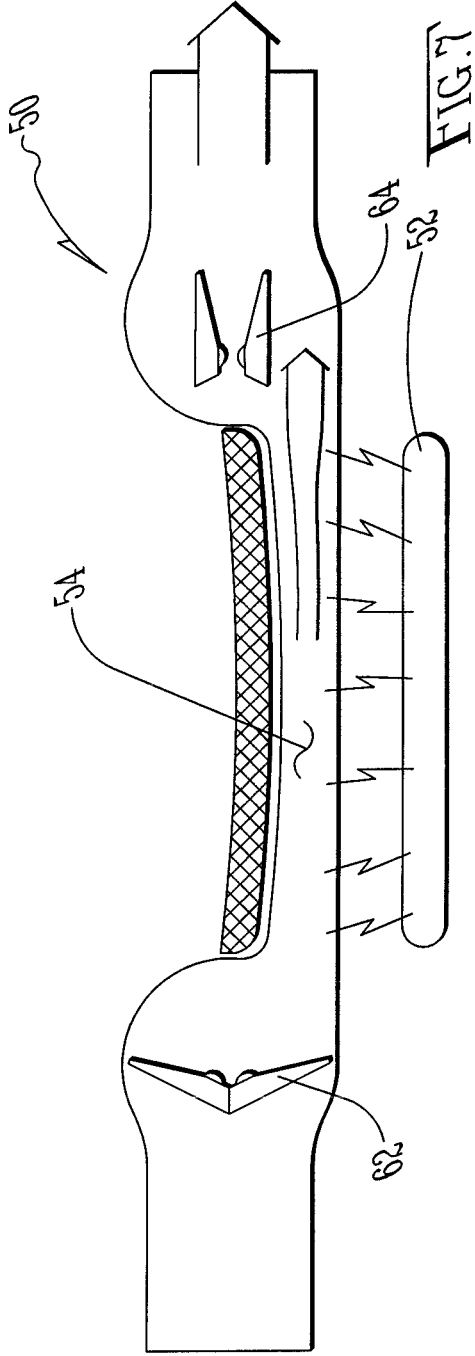
FIG. 6
FIG. 7

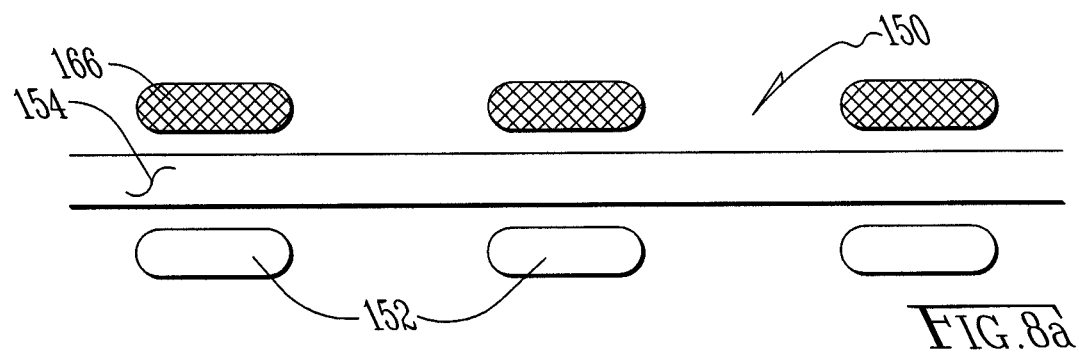
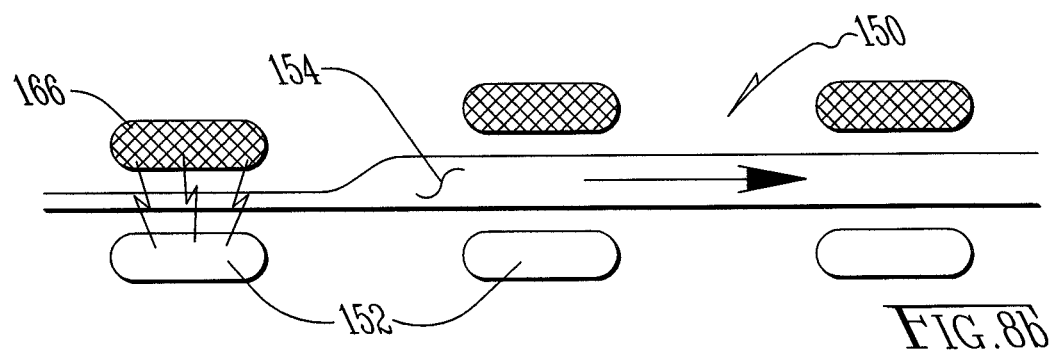
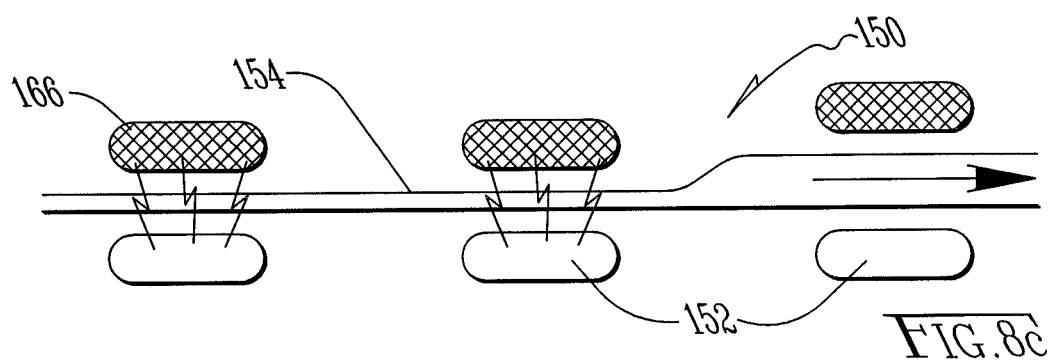

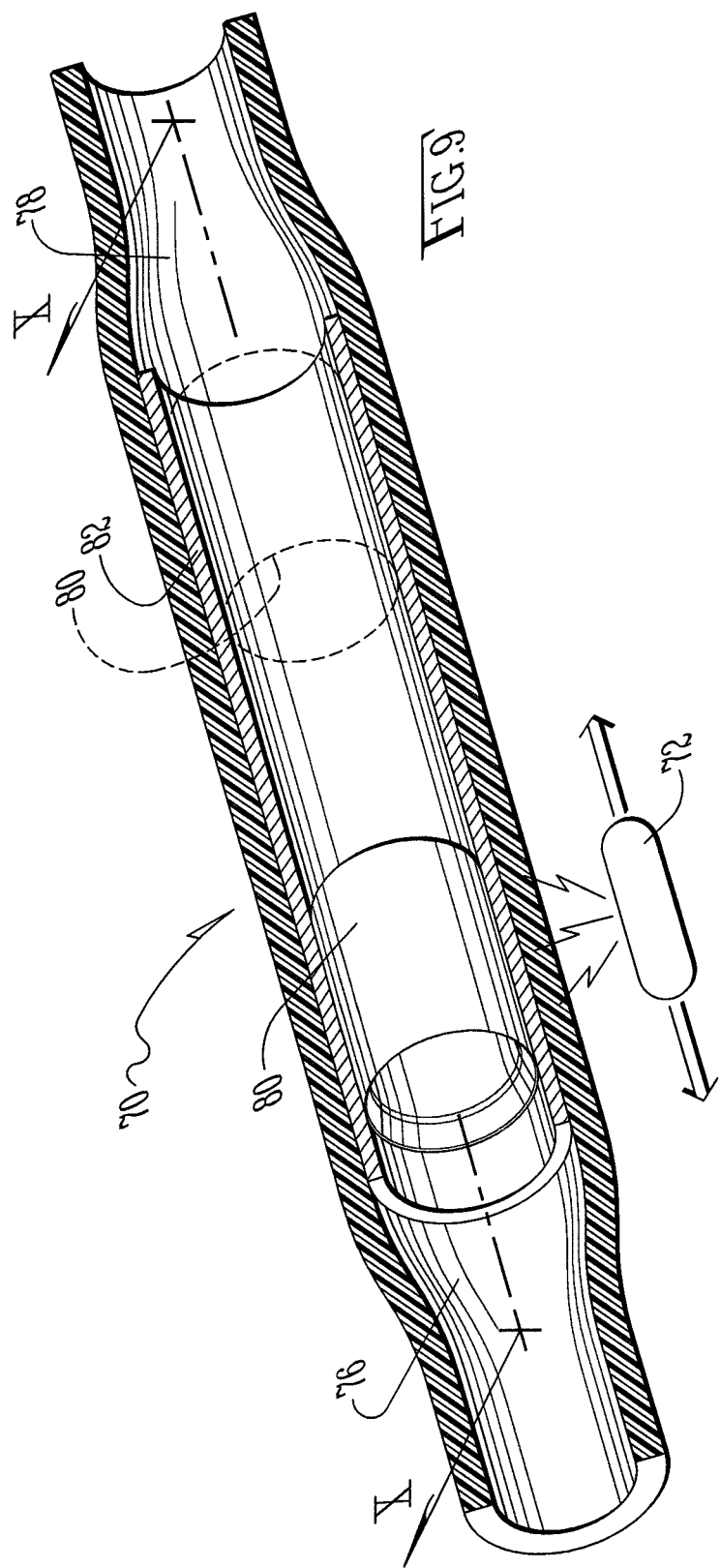

SUBCUTANEOUS FLUID PUMP

CROSS-REFERENCE TO RELATED APPLICATION(S)

This application is a continuation of U.S. patent application Ser. No. 14/019,000, filed Sep. 5, 2013; which claims the benefit of U.S. Provisional Application No. 61/743,527, filed Sep. 6, 2012; U.S. Provisional Application No. 61/744,177, filed Sep. 20, 2012; and, U.S. Provisional Application No. 61/797,291, filed Dec. 3, 2012, and, wherein the foregoing patent disclosures are incorporated herein by this reference thereto.

BACKGROUND AND SUMMARY OF THE INVENTION

The invention relates to medical procedures and, more particularly, to a subcutaneous fluid pump for a living patient that drains excess fluid from a first location and discharges into a second location, such as and without limitation the patient's bladder and/or stomach.

A number of additional features and objects will be apparent in connection with the following discussion of the preferred embodiments and examples with reference to the drawings.

BRIEF DESCRIPTION OF THE DRAWINGS

There are shown in the drawings certain exemplary embodiments of the invention as presently preferred. It should be understood that the invention is not limited to the embodiments disclosed as examples, and is capable of variation within the scope of the skills of a person having ordinary skill in the art to which the invention pertains. In the drawings.

FIG. 6 is a longitudinal section view comparable to FIG. 3 and showing the intake stroke comparable to FIG. 4;

FIG. 7 is a longitudinal section view comparable to FIG. 6 and showing the pumping stroke of FIG. 5;

FIG. 9 is a perspective view of an alternate embodiment of a subcutaneous pump in accordance with the invention;

DETAILED DESCRIPTION OF THE PREFERRED EMBODIMENTS

Figure 1:
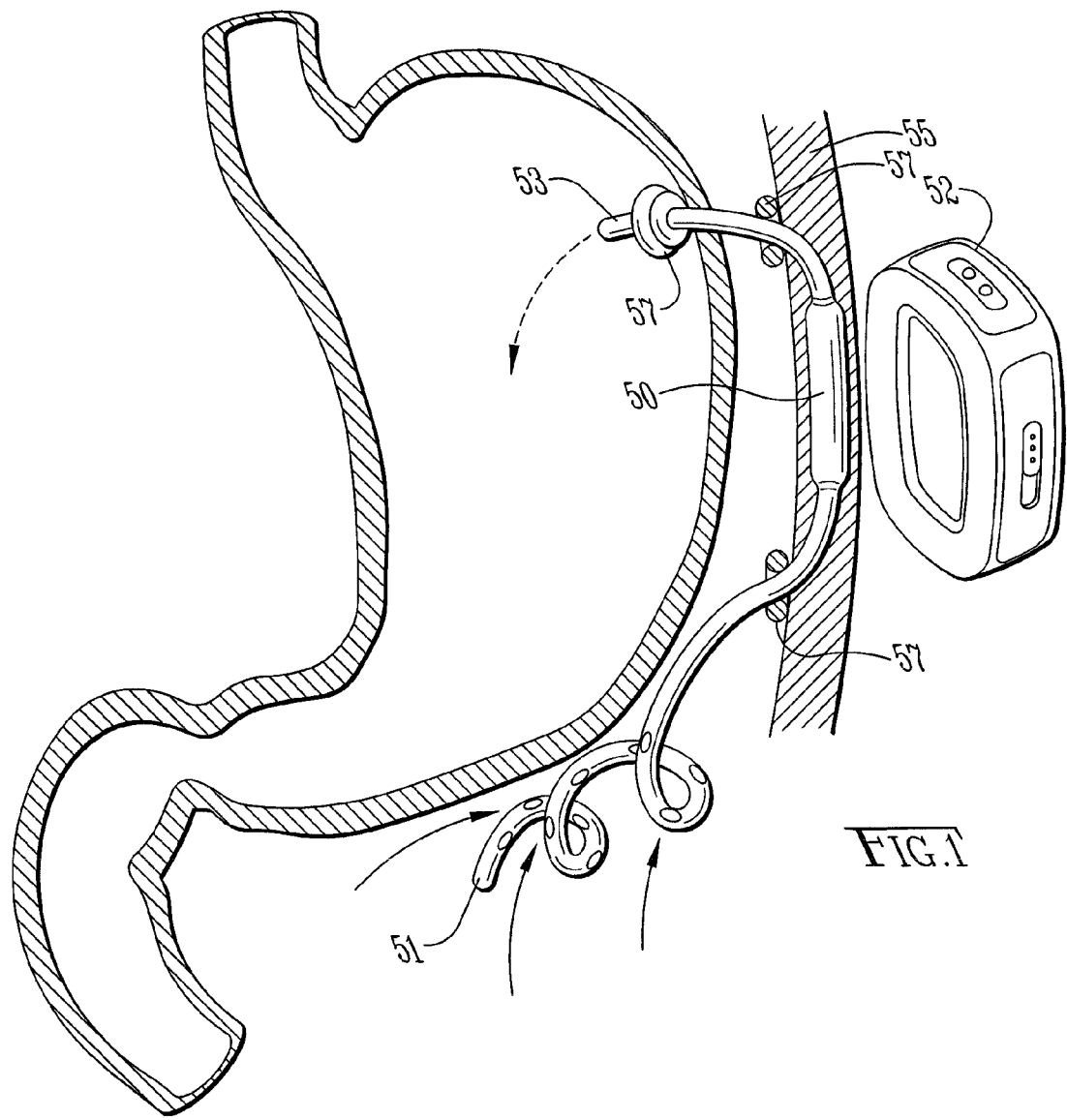
FIG. 1 is a stylized abdominal section view showing a subcutaneous pump and its controller in accordance with the invention, wherein portions of a human abdomen are shown to illustrate the preferred embedded location therefor.
Figure 2:
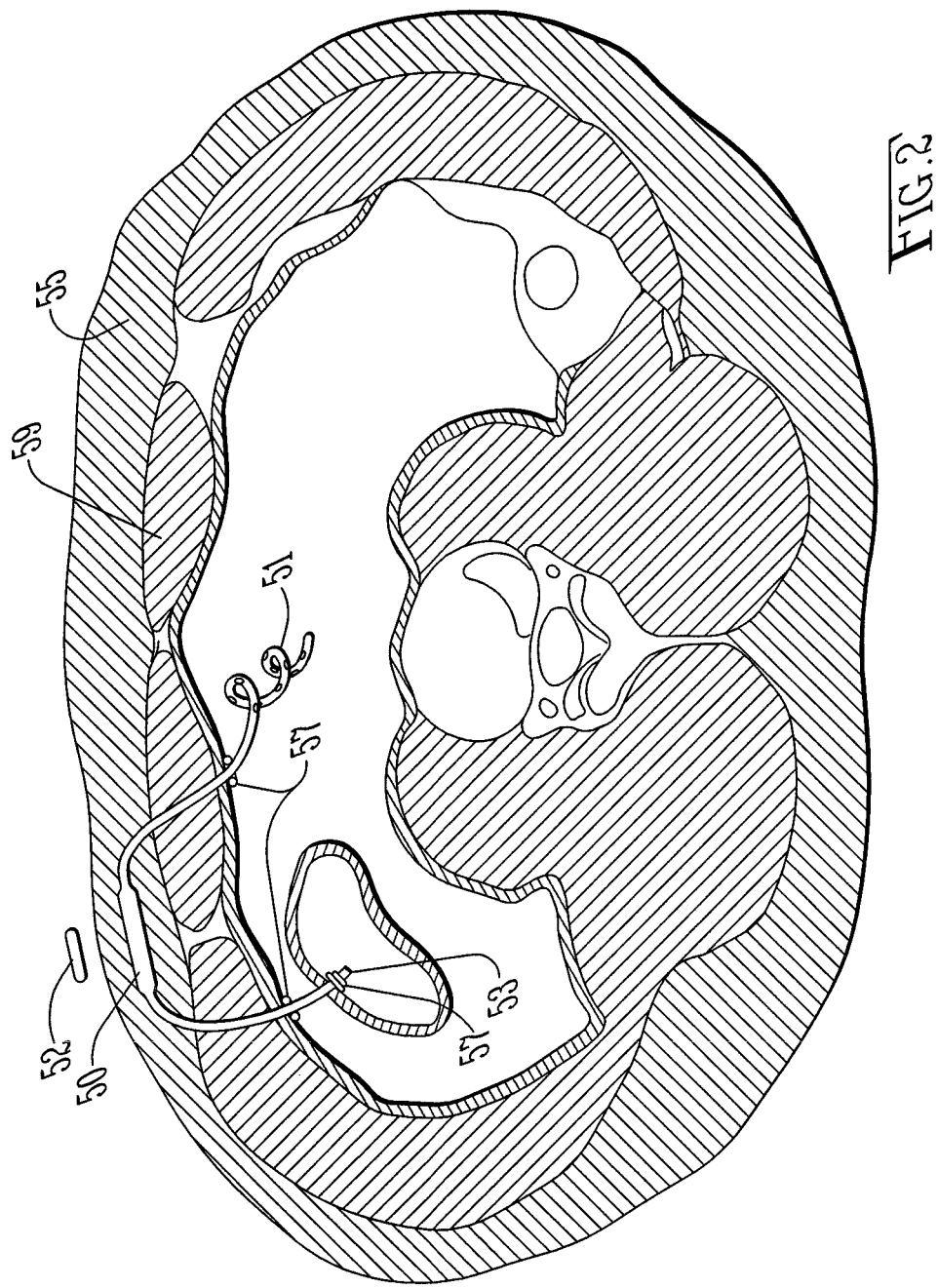
FIG. 2 is an abdominal section view comparable to FIG. 1 except taken through or near to the transpyloric plane.
Figure 3:
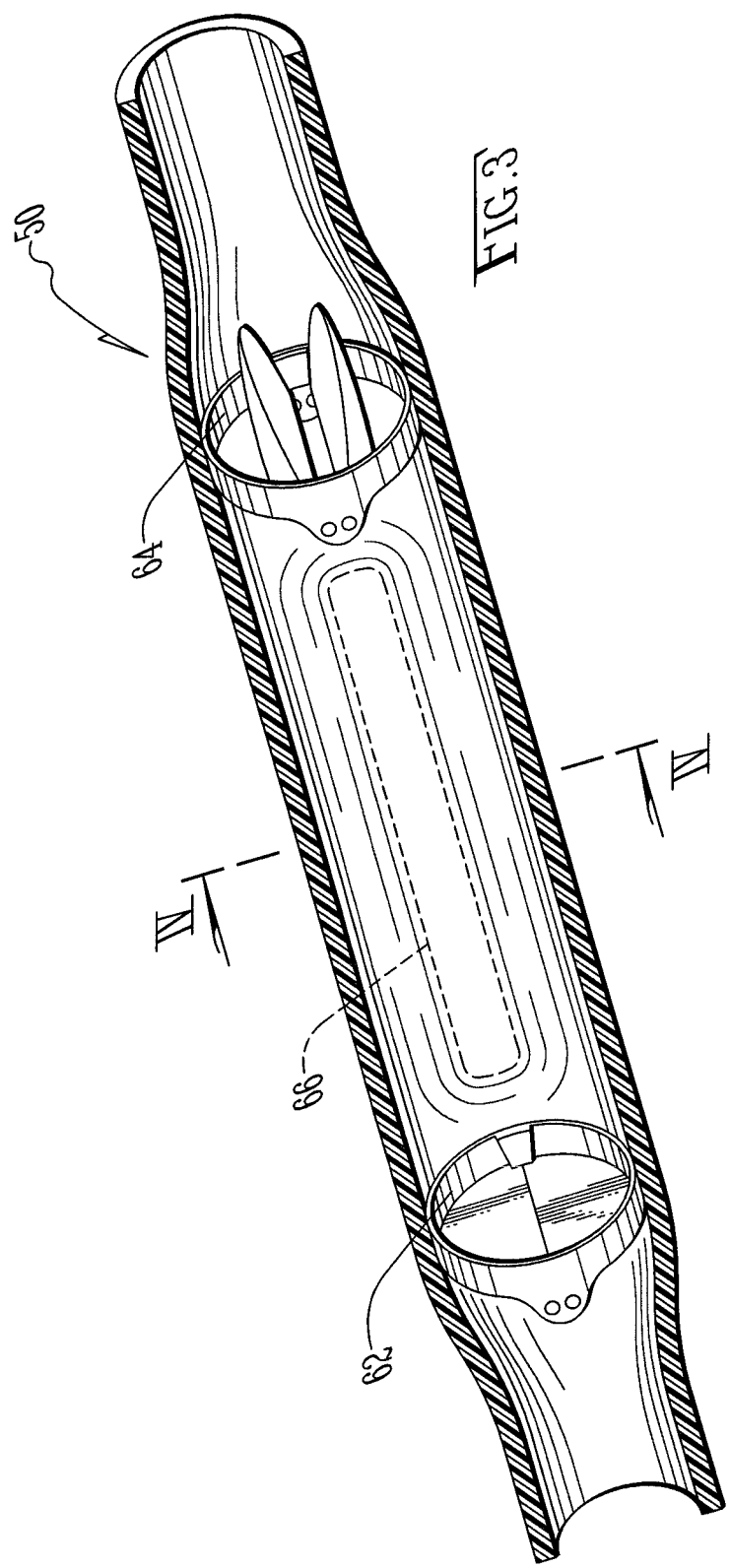
FIG. 3 is a longitudinal section view of the FIG. 1 pump on an enlarged scale.

FIGS. 1 through 7 show a first embodiment of a subcutaneous pump 50 in accordance with the invention, along with its controller 52. In this example use environment, the pump 50 is implanted inside the abdomen of a patient, and will drain excess fluid from a first location, then discharge the excess fluid in a second location. As shown in FIGS. 1 and 2, the second location is a stomach.

More particularly, the pump 50 is housed in a single continuous length of flexible tubing from the fenestrated intake end 51 left loose in the peritoneal cavity to the discharge end 53 spilling into the stomach. There are many suitable polymer materials for such flexible tubing. Again, aside from some optional O-rings 57 or other sort of clips or retainers, the pump 50 is housed in a single continuous length of flexible tubing.

Hence the pump portion 50 of the tubing is merely a specified medial zone in the tubing and flanked by one length of tubing which forms the fenestrated intake end 51 and an another length of tubing that terminates in the discharge end 53. The flanking lengths of tubing are not required to be and will not likely be the same length. Indeed, it is expected that the fenestrated intake end 51 will be the relatively lengthier length of tubing.

It is aspect of the invention to embed the specified zone of the tubing that houses the inner workings of the pump 50 in the subcutaneous layer 55 of the patient's abdominal wall. Preferably the pump portion 50 is disposed entirely within the subcutaneous layer 55 only (which is approximately the same as the skin and superficial fascia layer). Preferably the pump portion 50 is not placed at the interface between the subcutaneous layer 55 and muscle 59.

The flanking tube ends will penetrate out of the subcutaneous layer 55 on opposite ends of the pump. The fenestrated intake end 51 will be disposed dangling loosely in the peritoneal cavity. The discharge end will transit the peritoneal cavity and the gastric wall to be disposed discharging into the stomach. Optional retainers 57 or other sort of fasteners may be used to hold things in position.

FIG. 3-7 shows that this pump 50 is a form of a positive displacement pump. The pump 50 has a plenum 54, the plenum 54 extends longitudinally between an inlet check valve 62 and an outlet check valve 64, respectively.

In at least the general description above, this pump 50 share similarities with a pumping steam trap as disclosed by for example U.S. Pat. No. 5,938,409—Radle, Jr. et al.

However, in the subcutaneous pump 50 in accordance with the invention it is desirable to use medical grade check valves designed for implant use, such as and without limitation the artificial heart valve disclosed by U.S. Pat. No. 5,397,347—Cuilleron et al. Check valves such as these open and close under very low pressure gradients.

The plenum 54 has a sidewall and affixed on or in the sidewall is an elongated strip 66 of material that responds to an applied magnetic field. Such material may be referred to as magnetic or magnetizable material. The material of the strip 66 need not be a permanent magnet, but it does need to respond to an applied magnetic field. FIG. 1 and shows that controller 52 is preferably worn on the patient's body just outside a very close location to the subcutaneous pump 50. The controller 52 is configured to provide a fluctuating magnetic field to make the pump 50 operate without having to have a physical link.

Figure 4:
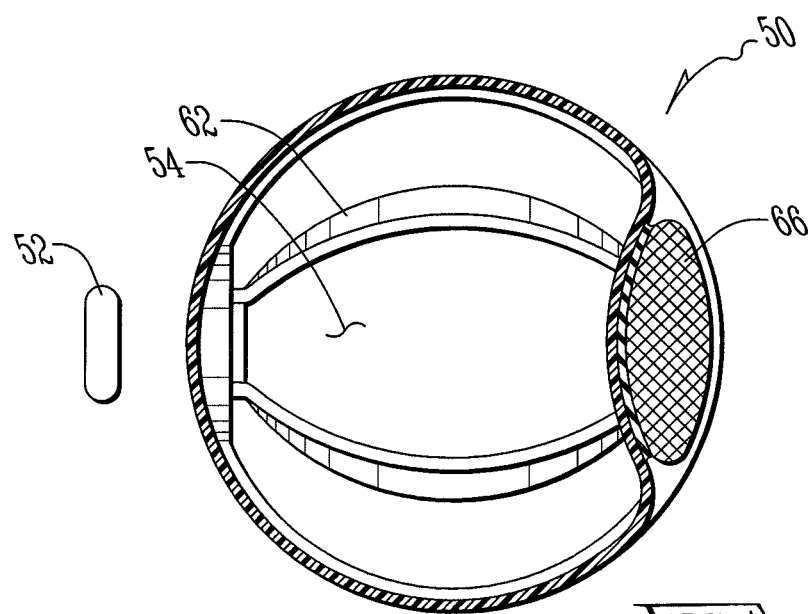
FIG. 4 is an enlarged scale sectional view taken along the cutting line IV-IV in FIG. 3.
Figure 5:
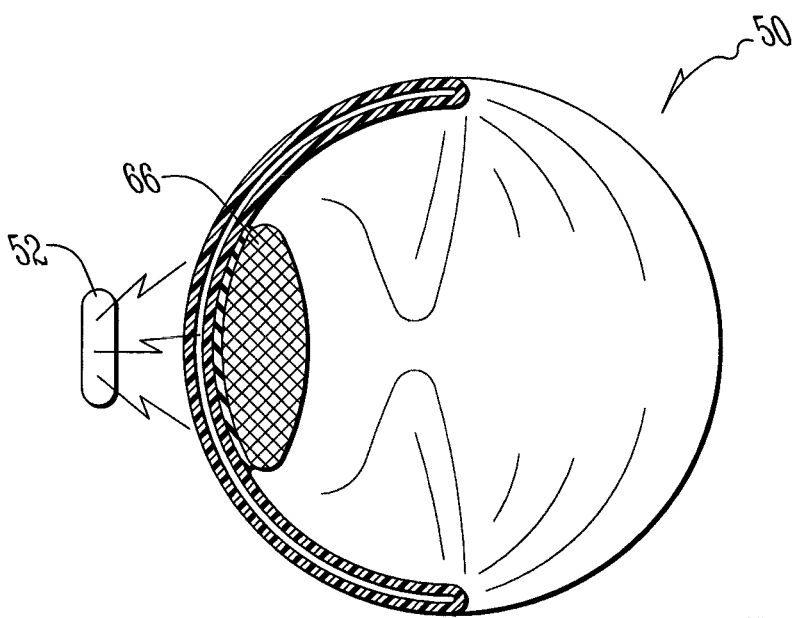
FIG. 5 is a sectional view comparable to FIG. 4 except showing the pump having undergone a pumping stroke.

FIG. 4 is a cross-section view through the plenum 54 and strip 66 in the absence of an applied magnetic field. FIG. 6 is a counterpart longitudinal section view. The pump portion 50 of the flexible tubing has sufficient shape memory to more or less restore the plenum 54 to a more or less cylindrical shape after every cycle of being deformed to a collapsed state. FIGS. 5 and 7 show the application of a magnetic field by the controller 52. The strip 66 will be induced to move toward the arc of the sidewall that is 180° opposite from the strip 66, hence causing the plenum 54 to collapse. The end of the pumping stroke is shown by FIGS. 5 and 7.

When the plenum collapses as in FIGS. 5 and 7, the fluid inside the plenum 54 initially rises so slightly in pressure. But the pressure rise is sufficient to pressurize the inlet check valve 62 to CLOSE and concurrently as to pressurize the outlet check valve 64 to OPEN. As the plenum 54 collapses further, a volume of fluid is pumped out the outlet check valve 64 as it remains open. The pumping stroke produces a pumped pulse of fluid corresponding to a substantial fraction of the plenum 54's volume at its maximum open volume.

FIGS. 4 and 6 show the effect when the controller 52 performs a control action which corresponds to an intake stroke. The controller 52 might just switch OFF the applied field, and the plenum 54 might have enough inherent shape memory that it will restore itself to the shape shown in FIGS. 4 and 6. Alternatively, the controller 52 might apply a magnetic field with different properties, such as reverse polarity, to drive the strip 66 and/or plenum 54 open.

This will cause the collapsed, minimized volume of the plenum 54 to open up. With the volume increasing, the fluid pressure in the plenum 54 will initially drop slightly in pressure, causing a slight suction pressure. This activity will suction the outlet check valve 64 to CLOSE and suction the inlet check valve 82 62 to OPEN. Hence the result is an intake stroke.

Needless to say, the pump 50 follows an intake stroke with another pumping stroke, and so on, indefinitely as the controller 52 is configured or operated to do so.

The controller 52 produces a small magnetic field to cause the pump 50 to pump. Preferably but not to exclusion of alternatives, the controller comprises electromagnets that preferably operate on DC power which are believed to requires material cores (ie., not air cores like AC electromagnets). The DC electromagnets can have either permanent magnet cores or else magnetic and/or magnetizable cores.

It is believed that the strength of the magnetic field can be fairly weak, partly due to the close physical proximity between the controller 52 and the reactive strip 66. A weak magnetic field so that the patient travel normally without being a source of magnetic interference of too many electric products or devices, belonging to the patients or others.

Also, no doubt the modern world is filled with all sorts of magnetic fields produced from all sorts of consumer devices (eg., televisions) to municipal, industrial and commercial security systems (eg., RFID readers beside protected doorways). It is believed that such fields may interfere with the subcutaneous pump 50. However, it is also believed that the interference in most cases will be temporary, and, not life threatening to the patient.

Unlike a heart valve, where the patient doesn't want to miss a beat, a patient with this subcutaneous pump should thrive for limited periods of inoperativeness of the pump.

It is a further aspect of the invention that the pump 50 in accordance with the invention is left permanently disposed in the subcutaneous layer of the patient. The controller 52 is designed to provide control signals, to provide feedback to the patient such as for inoperativeness because of interference from an external magnetic field, and other features too. For example, the controller 52 might be configured not only to move the strip 66 between flexion and extension, but also sense the position of the strip 66. That way, the controller 66 can detect the operativeness of the strip 66, as well as estimate flow capacity. Moreover, the controller 52 might be configured to accepts inputs from other detectors (none shown) that might relate to a data signal for calculating a speed-up or slow-down of flow capacity. Additionally, the battery-life for the controller 52 is dependent on batteries in the controller 52, which are readily accessible by the patient or assistants.

FIG. 8 comprises a series of sectional views FIGURES (a) through (f) of another embodiment of a subcutaneous pump 150 in accordance with the invention. This pump 150 has a peristaltic pumping action. This pump 150 has a plenum 154 of flexible tubing as before. Preferably the plenum 154 has shape memory such that in the absence of a magnetic field, the plenum 154 self-restores its open lumen to a cylindrical shape or the like (eg., an axial hollow shape). In contrast to before, this pump 150 has no check valves. This pump 150 does have a plurality axially-spaced reactive strips 166 as well as a plurality of axially-spaced, localized sources 152 of magnetic fields. Preferably these localized sources 152 can be switched ON and OFF according to a predetermined sequence by an overall controller (eg., in housing 52 as shown in FIG. 1).

Figure 8D:
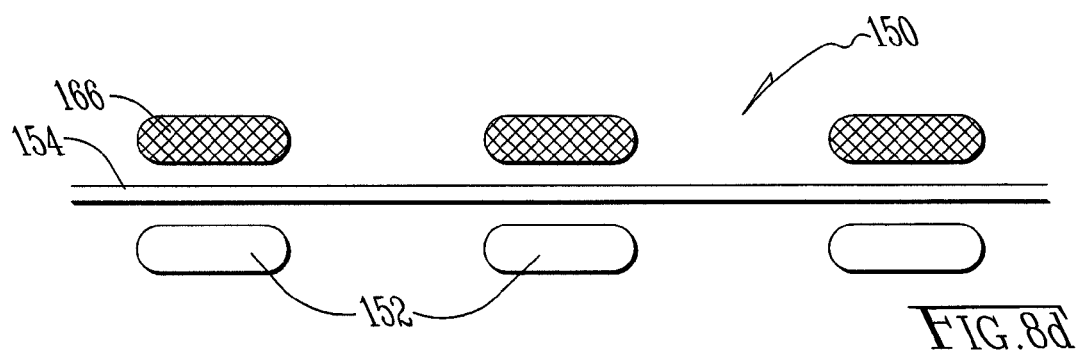
FIG. 8 comprises a series of sectional views FIGS. 8(a) through 8(f) of another embodiment of a subcutaneous pump in accordance with the invention, which pump has a peristaltic pumping action.

FIG. 8(a) shows all the localized sources switched OFF. The plenum 154 is wide open. FIGS. 8(b) through 8(d) show all the localized sources 152 progressively switching ON from the intake end (eg., the left end in the view) to the outlet end (eg., the right end in the view) to cause the original volume of fluid in the wide open plenum 154 to be squeezed through the outlet (eg., the right end of the view). The foregoing comprises the pumping stroke.

Figure 8E:
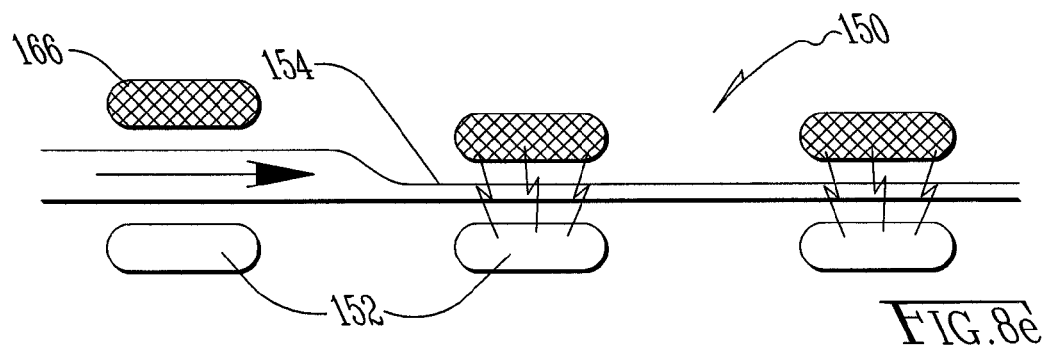
Figure 8F:
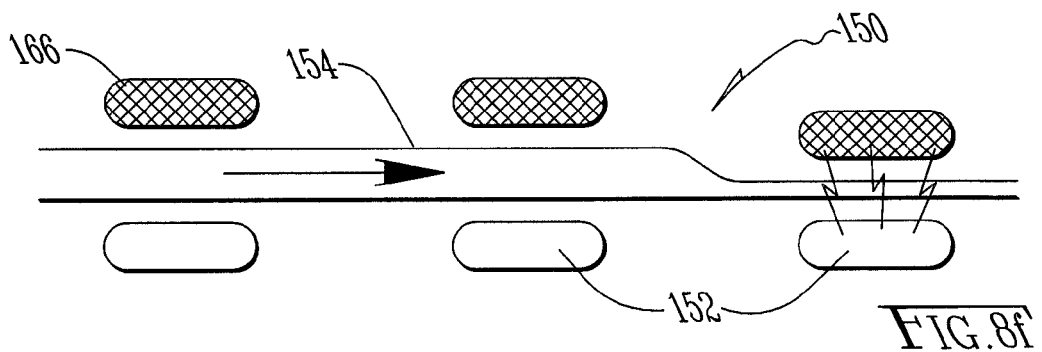

The preferred manner of intake stroke in FIGS. 8(e), 8(f) and 8(a). All the localized sources 152 progressively switch OFF from the intake end (eg., the left end in the view) to the outlet end (eg., the right end in the view) to the progressively opening plenum to suction in a new volume of fluid from the inlet (eg., the left end of the view).

FIG. 9 shows an alternate embodiment of a subcutaneous pump 70 in accordance with the invention. This pump 70 has a plenum 74 extending between and an inlet 76 and outlet 78, and also has a miniature slide 80 contained inside the plenum 74 and given the freedom of movement to reciprocate between the inlet 76 and outlet 78. The slide 80 slides in a slideway 82.

The slide 80 is preferably made of a material that responds to an applied magnetic field. The material of the slide 80 need not be a permanent magnet, but it does need to respond to an applied magnetic field. Here, the controller 72 reciprocates the slide 80 between a position shown in solid line for it, to a position shown in dashed lines.

The solid line location of the slide 80 corresponds to about the end of its intake stroke. The dashed line location of the slide 80 corresponds to about the end of its pumping stroke.

Figure 10:
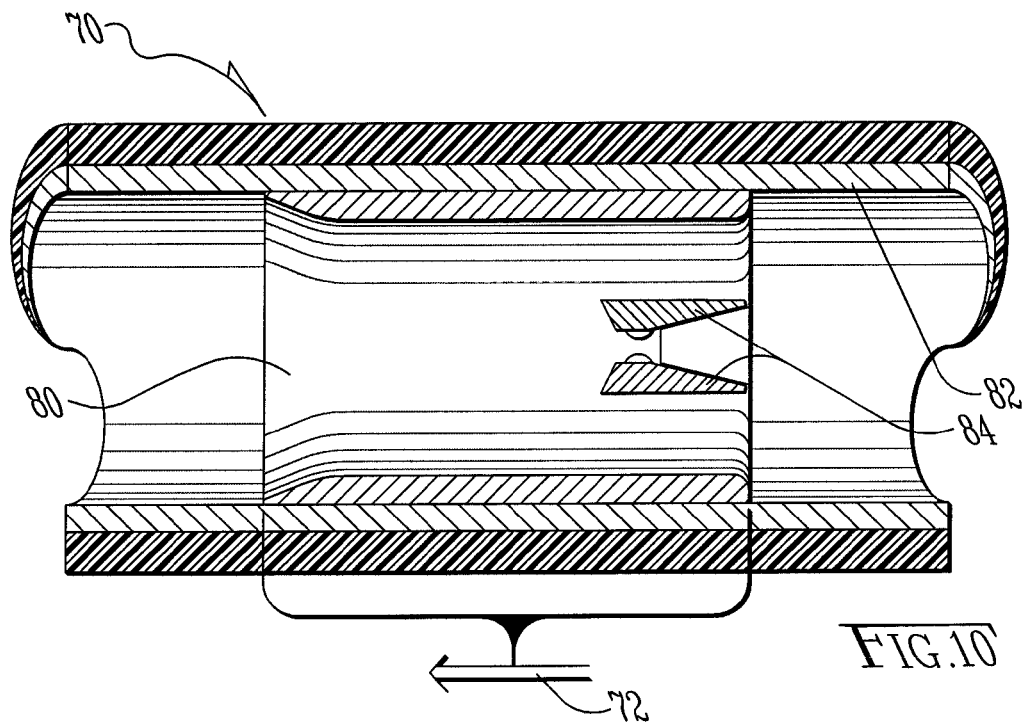
FIG. 10 is an enlarged scale sectional view taken along the cutting line X-X in FIG. 9, and showing the pump during an intake stroke.
Figure 11:
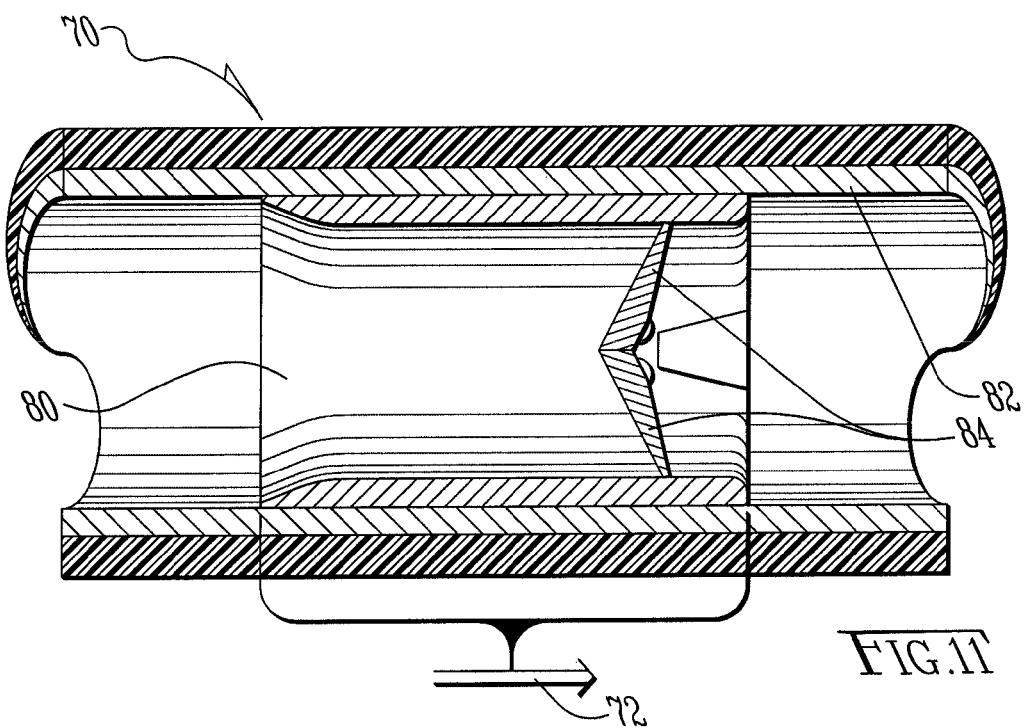
FIG. 11 is a sectional view comparable to FIG. 10 except showing the pump during a pumping stroke.

FIG. 10 shows that this embodiment of the pump 70 only has a single check valve 84. The lone check valve 84 is mounted in the slide 80. As the slide 80 is driven towards the intake end (eg., the left in this view), the check valve 84 is open glides through the fluid that fills the plenum 74. FIG. 11 shows the check valve 84 being driven toward the outlet 78 end. Here the single check valve 84 shuts, and the fluid in the plenum 74 is pumped out the outlet 78. At the same time, however, fluid from the feed pipes is being suctioned in through the inlet 76 to back fill the plenum 74 as the slide 80 is driving at the former volume of fluid that last occupied the plenum 74.

Figure 12:
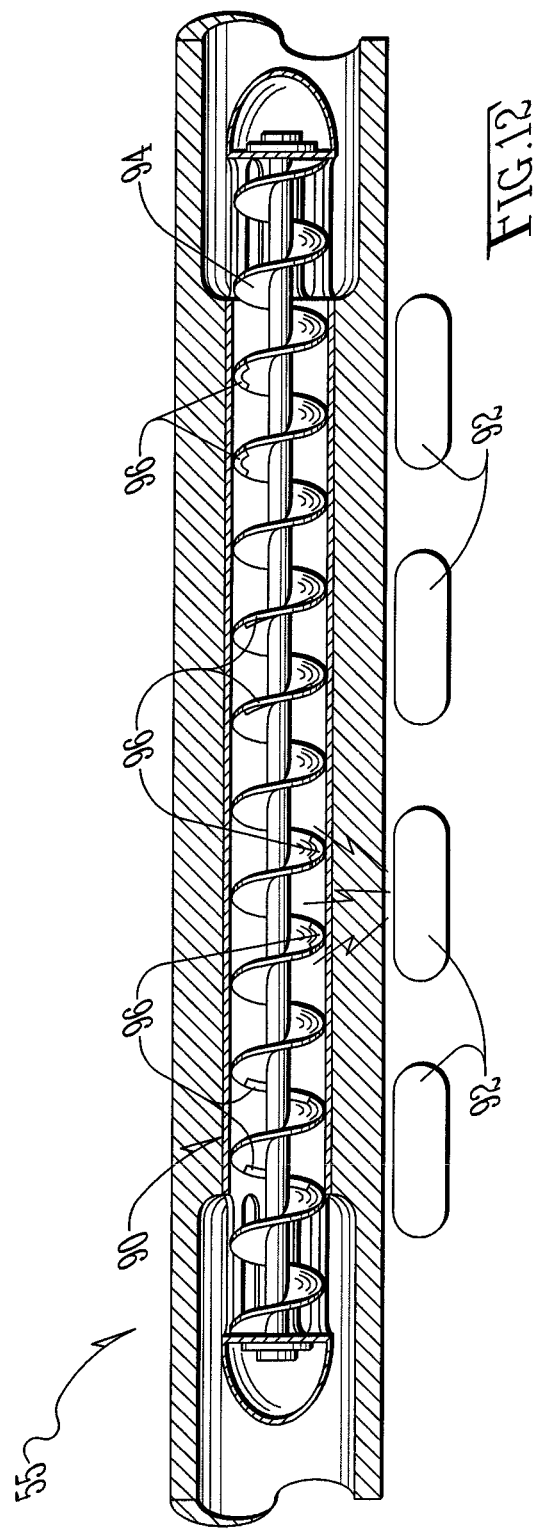
FIG. 12 is a perspective view of an additional embodiment of a subcutaneous pump in accordance.

FIG. 12 is a perspective view of an additional embodiment of a subcutaneous pump 90 in accordance. Again, the pump 90 is a specified zone of single continuous piece of flexible tubing between and intake end and a discharge end (eg., see FIGS. 1 and 2, but not shown in this view). The intake end is disposed inside the peritoneal cavity. The discharge end is disposed inside some other target location like the stomach or bladder.

The specified zone of the pump 90 which contains the inner workings of the pump 90 is embedded in the subcutaneous layer 55 of the patient's abdominal wall. Preferably the pump portion 90 is disposed entirely within the subcutaneous layer 55 only (which is approximately the same as the skin and superficial fascia layer). Preferably the pump portion 90 is not placed at the interface between the subcutaneous layer 55 and muscle.

This pump 90 has a plenum and inside the plenum is an elongated miniature auger 94. Like the FIG. 8 embodiment, this pump 90 has a plurality axially-spaced reactive strips 96 as well as a plurality of axially-spaced, localized sources 92 of magnetic fields. Preferably these localized sources 92 can be switched ON and OFF according to a predetermined sequence by an overall controller (eg., as housed inside a housing 52 as shown in FIG. 1).

The reactive strips 66 are placed on the outer edge of the helical flight of the auger 94 at axially-spaced locations, and, at respectfully angularly-distributed locations as well. Here, there are four (4) such axial strips 66 and each succeeding one is rotated 90° (ninety degrees) counter-clockwise from the preceding strip 66. Each localized source 92 can be energized one at a time such that the localized source 92 locks on its respective axial counterpart reactive strip 66 and pulls the strip 66 closest to the wall to the source 92.

For example, in FIG. 12, the magnetic-field source 92 second from left is energized (the are switched OFF), and, it has pulled the reactive strip 96 also second from the left straight down to the six o'clock position.

The next sequence of events would be switching OFF the source second from left and switching ON concurrently the source third from left. This will index the helical flight of the auger 94 around by 90° (ninety degrees).

Switching OFF the source third from left concurrently while switching ON the source fourth from left (eg., the one on the end on the right) will index the helical flight of the auger 94 around by 90° (ninety degrees).

Switching OFF the source fourth from left concurrently while switching ON the source first on the left will index the helical flight of the auger 94 around by 90° (ninety degrees). And so on, that by the time the condition is returned to as shown in FIG. 12, the auger will have rotated 90°. The rotation of the auger need not be continuous. It can be in steps.

Preferably, the helical flight of the auger 94 as well as the rest of the auger assembly (excluding the reactive strips 96) are preferably made of non-magnetic materials.

The invention having been disclosed in connection with the foregoing variations and examples, additional variations will now be apparent to persons skilled in the art. The invention is not intended to be limited to the variations specifically mentioned, and accordingly reference should be made to the appended claims rather than the foregoing discussion of preferred examples, to assess the scope of the invention in which exclusive rights are claimed.

What is claimed is:

1. A subcutaneous pump configured to drain excess fluid from a first bodily location in a patient and discharges into a second bodily location, comprising:
   elongated flexible tube having a sidewall extending between an intake end for leaving loose in the first location, and, a discharge end for discharging the excess patient fluid in the second location, wherein said elongated flexible tube defines a central lumen;
   said elongated flexible tube having a specified medial zone adapted to be embedded in the subcutaneous layer of the patient's abdominal wall;
   said central lumen of said elongated flexible tube in the specified medial zone comprising a plenum all within the specified medial zone and axially extending between a relative inlet portion and an axially spaced apart relative outlet portion;
   wherein the sidewall of said elongated flexible tube in the specified medial zone has axially-extending, angularly delimited zones comprising at least a proximal angularly delimited zone configured to face the patient's skin and a distal angularly delimited zone configured to face the patient's first and/or second bodily locations;
   an elongated strip of magnetic or magnetizable material affixed on or in the either proximal angularly delimited zone of the sidewall of said elongated flexible tube or else the distal angularly delimited zone of the sidewall of said elongated flexible tube;
   whereby a fluctuating magnetic field causes the sidewall of said elongated flexible tube in the specified medial zone to distort the plenum.

2. The subcutaneous pump of claim 1, wherein:
   the elongated strip of magnetic or magnetizable material are affixed on or in the distal angularly delimited zone of the sidewall of said elongated flexible tube;
   whereby an applied magnetic field causing attraction of the elongated strip of magnetic or magnetizable material will consequently cause the collapse of the plenum.

3. The subcutaneous pump of claim 2, further comprising:
   an intake check valve disposed inside the tube proximate the relative intake portion of the plenum.

4. The subcutaneous pump of claim 3, further comprising:
   an outlet check valve disposed inside the tube proximate the relative outlet portion of the plenum.

5. The subcutaneous pump of claim 2, further comprising:
   an outlet check valve disposed inside the tube proximate the relative outlet portion of the plenum.

6. The subcutaneous pump of claim 4, further comprising:
   a remote source of an applied magnetic field outside of the patient's body and proximate the specified medial zone;
   a correspondingly remote controller for said magnetic field source;
   wherein when the controller comprises first and second states;
   the first state comprises energizing the magnetic field source to create an applied magnetic attraction force on the elongated strip of magnetic or magnetizable material, wherein the plenum collapses and whereby corresponding to a pumping stroke.

7. The subcutaneous pump of claim 6, further comprising:
   the second state comprises switching the magnetic field source OFF.

8. The subcutaneous pump of claim 7, wherein:
   the second state comprises switching the magnetic field source to create an applied magnetic repulsion force on the elongated strip of magnetic or magnetizable material, wherein the plenum restores to being an open central lumen generally ranging from a cylindrical shape to at least an axially hollow shape, and whereby corresponding to an intake stroke.

9. A subcutaneous pump configured to drain excess fluid from a first bodily location in a patient and discharges into a second bodily location, comprising:
   elongated flexible tube having a sidewall extending between an intake end for leaving loose in the first location, and, a discharge end for discharging the excess patient fluid in the second location, wherein said elongated flexible tube defines a central lumen;
   said elongated flexible tube having a specified medial zone adapted to be embedded in the subcutaneous layer of the patient's abdominal wall;
   said central lumen of said elongated flexible tube in the specified medial zone comprising a plenum all within the specified medial zone and axially extending between a relative inlet portion and an axially spaced apart relative outlet portion;
   wherein the sidewall of said elongated flexible tube in the specified medial zone has axially-extending, angularly delimited zones comprising at least a proximal angularly delimited zone configured to face the patient's skin and a distal angularly delimited zone configured to face the patient's first and/or second bodily locations;
   a series of axially spaced elements of magnetic or magnetizable material affixed on or in the either proximal angularly delimited zone of the sidewall of said elongated flexible tube or else the distal angularly delimited zone of the sidewall of said elongated flexible tube;
   whereby a repetitive, axially progressing applied magnetic field starting from the relative intake portion to the relative outlet portion, and then starting over at the relative intake portion, causes the sidewall of said elongated flexible tube in the specified medial zone to distort the plenum in a peristaltic action.

10. The subcutaneous pump of claim 9, wherein:
    the series of axially spaced elements of magnetic or magnetizable material are affixed on or in the distal angularly delimited zone of the sidewall of said elongated flexible tube;
    whereby a repetitive, axially progressing applied magnetic field causing axially progressive magnetic attraction of the series of axially spaced elements of magnetic or magnetizable material will consequently cause the progressive collapse of the plenum from the relative intake portion to the relative outlet portion, whereby resulting in a peristaltic pumping action.

11. The subcutaneous pump of claim 10, further comprising:
    a remote source of an applied magnetic field outside of the patient's body and proximate the specified medial zone;
    a correspondingly remote controller for said magnetic field source;
    wherein when the controller comprises first and second states;
    the first state comprises energizing the magnetic field source to create an axially progressive magnetic attraction field on the series of axially spaced elements of magnetic or magnetizable material, progressing from the relative intake portion to the relative outlet portion.

12. The subcutaneous pump of claim 11, further comprising:
    the second state comprises progressively de-energizing the magnetic field to OFF from the relative intake portion to the relative outlet portion.

13. The subcutaneous pump of claim 11, wherein:
    the second state comprises progressively energizing the magnetic source to create an axially progressive magnetic repulsion field on the series of axially spaced elements of magnetic or magnetizable material from the relative intake portion to the relative outlet portion, causing the collapsed plenum to progressively restore from the relative intake portion to the relative outlet portion to being an open central lumen generally ranging from a cylindrical shape to at least an axially hollow shape, and whereby corresponding to an intake stroke.

14. A subcutaneous pump configured to drain excess fluid from a first bodily location in a patient and discharges into a second bodily location, comprising:
    elongated flexible tube having a sidewall extending between an intake end for leaving loose in the first location, and, a discharge end for discharging the excess patient fluid in the second location, wherein said elongated flexible tube defines a central lumen;
    said elongated flexible tube having a specified medial zone adapted to be embedded in the subcutaneous layer of the patient's abdominal wall;
    said central lumen of said elongated flexible tube in the specified medial zone comprising a plenum all within the specified medial zone and axially extending between a relative inlet portion and an axially spaced apart relative outlet portion;
    a reciprocating body of magnetic or magnetizable material disposed inside the plenum to reciprocate back and forth between the relative intake portion and relative outlet portion;
    whereby a magnetic field driving reciprocating body to reciprocate back and forth in the plenum causes a pumping action.

15. The subcutaneous pump of claim 14, further comprising:
    at least one check valve disposed any of:—
        inside the tube proximate the relative intake portion of the plenum;
        inside the tube proximate the relative outlet portion of the plenum; and/or
        wherein the reciprocating body has a flow passage formed therein or thereon, and therefore inside the flow passage of the reciprocating body.

16. The subcutaneous pump of claim 15, further comprising:
    a remote source of an applied magnetic field outside of the patient's body and proximate the specified medial zone;
    a correspondingly remote controller for said magnetic field source;
    wherein when the controller controls the magnetic field source to drive the reciprocating body to reciprocate back and forth between the relative intake portion and relative outlet portion.

* * * * *